_United States Patent_ [19]

Gryaznov et al.

[11] 3,931,345

[45] Jan. 6, 1976

[54] HYDROGENATION AND HYDRODEALKYLATION PROCESS

[76] Inventors: Vladimir Mikhailovich Gryaznov, Leninskie Gory MGU zona L, kv. 11; Viktor Sergeevich Smirnov, Kutuzovsky prospekt, 26, kv. 555; Alexandr Petrovich Mischenko, Khersonskaya ul., 7, korpus 4, kv. 515; Natalia Vsevolodovna Orekhova, Ul. Marii Ulyanovoi, 8, korpus 1, kv. 95; Boris Petrovich Krivdin, Belyaevo-Bogorod-skoe, kvartal 48, korpus 23, kv. 114; Viktoria Petrovna Polyakova, ul. Trofimova, 15 kv. 201; Evgeny Mikhailovich Savitsky, ul. Dmitria Ulyanova, DNR-3, kv. 13, all of Moscow, U.S.S.R.

[22] Filed: Apr. 6, 1973

[21] Appl. No.: 348,626

Related U.S. Application Data

[62] Division of Ser. No. 92,195, Nov. 23, 1970, Pat. No. 3,799,889.

[52] U.S. Cl. .............................. 260/667; 260/672 R
[51] Int. Cl.² ...................... C07C 5/10; C07C 3/58
[58] Field of Search ............................. 260/667, 672

[56] References Cited
UNITED STATES PATENTS

| 2,721,226 | 10/1955 | Ciapetta et al. | 260/667 |
| 2,890,114 | 6/1959 | Ruthardt et al. | 75/172 |
| 3,153,678 | 10/1964 | Logemann | 260/667 |
| 3,159,687 | 12/1964 | Lehman | 260/667 |
| 3,261,876 | 7/1966 | Kovach | 260/667 |
| 3,290,406 | 12/1966 | Pfefferle | 260/683.3 |
| 3,344,582 | 10/1967 | Merrill et al. | 55/16 |
| 3,562,346 | 2/1971 | Smirnov et al. | 260/673.5 |
| 3,595,932 | 7/1971 | Maslyansky et al. | 260/672 R |
| 3,607,961 | 9/1971 | Kovach | 260/672 R |
| 3,649,707 | 3/1972 | Lester | 260/672 R |

_Primary Examiner_—Delbert E. Gantz
_Assistant Examiner_—James W. Hellwege
_Attorney, Agent, or Firm_—Holman & Stern

[57] ABSTRACT

Hydrogenation and hydrodealkylation catalysts of aromatic hydrocarbons comprising a palladium alloy with molybdenum, containing from 0.1 to 30 percent by weight of molybdenum.

The catalyst can be manufactured in the form of powders, blacks, membranes, foils or tubes and employed in the processes of hydrogenation and hydrodealkylation of aromatic hydrocarbons carried out either separately or simultaneously.

14 Claims, No Drawings

HYDROGENATION AND HYDRODEALKYLATION PROCESS

This is a division of our copending application Ser. No. 92,195 filed Nov. 23, 1970 now U.S. Pat. No. 3,799,889 granted Nov. 26, 1974.

The present invention relates to the production of catalysts, and more particularly concerns catalysts for the hydrogenation and the hydrodealkylation of aromatic hydrocarbons. The invention may be applied in the production of monomers for the preparation of synthetic materials and other semi-products.

Catalysts industrially used for processing hydrocarbons are in the form of powders, blacks and granules and usually consist of two or more substances or are applied on a support, such as nickel, or platinum on aluminum oxide.

Such catalysts cannot be used as membrane catalysts, i.e. selectively permeable to hydrogen but which do not permit the carrying out of hydrogenation and hydrodealkylation processes simultaneously without mixing the starting materials. These processes are more effectively carried out with catalysts in the form of partitions selectively permeable only to hydrogen, so that on one side of the partition the process of splitting off of hydrogen will take place, and on the other, the process for the addition of hydrogen that has penetrated through the partition. Palladium alloys containing at least one other element from group VIII of the Periodic Table and also including copper, silver, gold and boron were suggested for such a partition (See French Pat. Nos. 1,579,529 and 1,586,678 and also British Pat. Nos. 1,199,683 and 1,234,855), in "a membrane catalyst".

The employment of the above-mentioned catalysts showed that they are of sufficient activity and selectivity.

It is an object of this invention to widen the variety of palladium catalysts available to be employed as a partition permselective to hydrogen and therefore to extend the application of such catalysts. A further object is to improve the heat-resistance of membrane catalysts.

This said and other objects of the invention are achieved by employing catalysts comprising an alloy of palladium with molybdenum. According to the invention the palladium alloy contains from 0.1 to 30 weight percent of molybdenum. More specific compositions are alloys containing from 2 to 15 weight percent of molybdenum.

The said catalysts can be employed as usual in the form of powders, blacks or gauzes and also as partitions, for example as membranes, films, foils and tubes permselective to hydrogen, for carrying out the hydrogenation, and hydrodealkylation processes.

The introduction of molybdenum into the alloy improves the heat-resistance of the catalyst, which is important in the heat-treatment when regenerating the catalyst.

Pure hydrocarbons or hydrocarbons diluted with a flow of nitrogen, argon or other gases that do not inhibit the applied catalyst may be used in the catalytic converting process.

Several examples are presented herein below for a better understanding of the invention. In all the examples the flow rate of the vaporised starting materials was 1.8 liter/hour. The analysis of the reaction products was carried out on a chromatograph.

EXAMPLE 1

Hydrogenation of Benzene

Hydrogenation of benzene to cyclohexane was carried out within a temperature range of from 190°–280°C in a hydrogen flow on a foil comprising a palladium alloy containing 2 weight percent of molybdenum. The weight of catalyst was 3.38 g. The apparent contact area is 66.8 cm$^2$. The cyclohexane yields according to temperature are presented in Table I.

| Temperature (°C) | Cyclohexane, mole % |
|---|---|
| 190 | 6.18 |
| 208 | 7.65 |
| 225 | 10.1 |
| 245 | 12.8 |
| 280 | 6.3 |

EXAMPLE 2

Hydrogenation of Benzene

Hydrogenation of benzene to cyclohexane was carried out within a temperature range of from 95°–220°C in a hydrogen flow on a foil comprising a palladium alloy containing 15 weight percent of molybdenum. The weight of the catalyst was 7.05 g, and the apparent contact area was 62 cm$^2$. The cyclohexane yields according to temperature are presented in Table II.

| Temperature (°C) | Cyclohexane, mole % |
|---|---|
| 97 | 26.6 |
| 140 | 30.9 |
| 155 | 42.9 |
| 163 | 49.7 |
| 170 | 50.7 |
| 177 | 53.4 |
| 185 | 62.3 |
| 200 | 72.0 |
| 210 | 84.1 |
| 220 | 71.0 |

EXAMPLE 3

Hydrodealkylation of Toluene

Hydrodealkylation of toluene to benzene was carried out within a temperature range of from 480°–610°C on a foil comprising a palladium alloy containing 2 weight percent of molybdenum. The weight of the catalyst was 3.38 g, and apparent contact area, 66.8 cm$^2$.

The benzene yields according to temperature are presented in Table III.

| Temperature (°C) | Benzene, mole % |
|---|---|
| 480 | 5.0 |
| 500 | 8.8 |
| 517 | 12.5 |
| 527 | 13.3 |
| 547 | 21.3 |
| 586 | 16.2 |

EXAMPLE 4

Hydrodealkylation of Toluene

Hydrodealkylation of toluene to benzene was carried out on the air-activated catalyst used in Example 3, comprising a palladium alloy containing 2 weight percent of molybdenum. The activation consisted in passing air through the reactor heated to 750°C for 1 hour at a flow rate of 2 liter/hour. The catalyst after being blown through with air was treated for 2 hours at 500°C with hydrogen fed at a flow rate of 1.8 liter/hour. The reaction was run at a temperature range of from 445°–590°C. The benzene yields according to temperature are presented in Table IV.

| Temperature (°C) | Benzene, mole % |
|---|---|
| 445 | 5.0 |
| 485 | 16.1 |
| 497 | 17.0 |
| 537 | 24.5 |
| 585 | 21.2 |
| 590 | 15.8 |

Comparison between the data of Table 3 and 4 shows that the described activation of the palladium-molybdenum catalyst doubles the benzene yield from toluene at a temperature of 500°C.

We claim:

1. In a method for the hydrogenation of aromatic hydrocarbons the improvement comprising reacting said hydrocarbons under hydrogenation conditions including a temperature of 100° to 300°C over a catalyst comprising a palladium-molybdenum alloy with a molybdenum content in the alloy of 0.1 to 30% by weight, said catalyst being in the form of granules, powder, or gauze, or membranes, films, foils or tubes selectively permeable only to hydrogen.

2. A method as claimed in claim 1 wherein said catalyst has a molybdenum content of 2 to 15% by weight.

3. A method as claimed in claim 1 wherein said catalyst has a palladium content of 98% by weight and a molybdenum content of 2% by weight.

4. A method as claimed in claim 1 wherein said catalyst has a palladium content of 85% by weight and a molybdenum content of 15% by weight.

5. A method as claimed in claim 1 wherein said hydrocarbons are fed together with hydrogen into a reactor with said catalyst.

6. A method as claimed in claim 1 wherein said hydrocarbons are fed in an inert gas flow into a reactor and hydrogen is fed by diffusion through said catalyst in the form of membranes, films, foils, or tubes.

7. A method as claimed in claim 2 wherein said hydrocarbon is benzene.

8. In a method for the hydrodealkylation of aromatic hydrocarbons, the improvement comprising reacting said hydrocarbons under hydrodealkylation conditions including a temperature of 400° to 650°C over a catalyst comprising a palladium-molybdenum alloy having a molybdenum content of 0.1 to 30% by weight in the form of granules, powder, or gauze or membranes, films, foils, or tubes that are selectively permeable only to hydrogen.

9. A method as claimed in claim 8 wherein said catalyst has a molybdenum content of 2 to 15% by weight.

10. A method as claimed in claim 8 wherein said catalyst has a palladium content of 98% by weight and a molybdenum content of 2% by weight.

11. A method as claimed in claim 8 wherein said catalyst has a palladium content of 85% by weight and a molybdenum content of 15% by weight.

12. A method as claimed in claim 8 wherein said aromatic hydrocarbons are fed together with hydrogen into a reactor with said catalyst.

13. A method as claimed in claim 8 wherein said hydrocarbons are fed in an inert gas flow and hydrogen is fed by diffusion through said catalyst in the form of membranes, tubes, foils, or films.

14. A method as claimed in claim 9 wherein said hydrocarbon is toluene.

* * * * *